(12) United States Patent
Lovley et al.

(10) Patent No.: US 11,823,808 B2
(45) Date of Patent: Nov. 21, 2023

(54) CONDUCTIVE COMPOSITE MATERIALS FABRICATED WITH PROTEIN NANOWIRES

(71) Applicant: University of Massachusetts, Boston, MA (US)

(72) Inventors: Derek R. Lovley, Amherst, MA (US); Todd Emrick, South Deerfield, MA (US); Yun-Lu Sun, Austin, TX (US); Brian Montz, Amherst, MA (US)

(73) Assignee: University of Massachusetts, Boston, MA (US)

( * ) Notice: Subject to any disclaimer, the term of this patent is extended or adjusted under 35 U.S.C. 154(b) by 1021 days.

(21) Appl. No.: 16/575,861

(22) Filed: Sep. 19, 2019

(65) Prior Publication Data

US 2020/0090830 A1    Mar. 19, 2020

Related U.S. Application Data

(60) Provisional application No. 62/733,496, filed on Sep. 19, 2018.

(51) Int. Cl.

| | |
|---|---|
| *H01B 1/12* | (2006.01) |
| *H01B 3/44* | (2006.01) |
| *H01B 5/14* | (2006.01) |
| *C12P 21/00* | (2006.01) |
| *C08L 83/04* | (2006.01) |

(Continued)

(52) U.S. Cl.
CPC .......... *H01B 1/12* (2013.01); *A61B 5/14539* (2013.01); *A61B 5/6801* (2013.01); *B82Y 5/00* (2013.01); *B82Y 30/00* (2013.01); *C07K 14/195* (2013.01); *C08L 29/04* (2013.01); *C08L 83/04* (2013.01); *C08L 89/00* (2013.01); *C09D 129/04* (2013.01); *C09D 183/04* (2013.01); *C12P 21/00* (2013.01); *H01B 3/44* (2013.01); *H01B 5/14* (2013.01); *A61B 2562/0285* (2013.01)

(58) Field of Classification Search
None
See application file for complete search history.

(56) References Cited

U.S. PATENT DOCUMENTS

| | | | |
|---|---|---|---|
| 7,498,155 | B2 | 3/2009 | Lovley et al. |
| 8,232,584 | B2 | 7/2012 | Lieber |

(Continued)

FOREIGN PATENT DOCUMENTS

| | | |
|---|---|---|
| CN | 1527051 A | 9/2004 |
| CN | 108365776 A | 8/2018 |

(Continued)

OTHER PUBLICATIONS

Lovley, "Electrically conductive pili: Biological function and potential applications in electronics," Science Direct, Current Opinion in Electrochemistry 2017, 4: 190-198.

(Continued)

*Primary Examiner* — Jeffrey D Washville
(74) *Attorney, Agent, or Firm* — Hamilton, Brook, Smith & Reynolds, P.C.

(57) ABSTRACT

Electrically conductive polymeric composite materials include microbially produced protein nanowires. The conductive composites are useful in diverse electronic materials applications, particularly in applications requiring biocompatibility, such as sensors and wearable electronics.

15 Claims, 6 Drawing Sheets

(51) Int. Cl.

| | |
|---|---|
| C08L 89/00 | (2006.01) |
| A61B 5/145 | (2006.01) |
| A61B 5/00 | (2006.01) |
| C08L 29/04 | (2006.01) |
| C07K 14/195 | (2006.01) |
| C09D 129/04 | (2006.01) |
| C09D 183/04 | (2006.01) |
| B82Y 30/00 | (2011.01) |
| B82Y 5/00 | (2011.01) |

(56) References Cited

U.S. PATENT DOCUMENTS

| | | | |
|---|---|---|---|
| 8,608,921 | B2 | 12/2013 | Li |
| 8,729,233 | B2 | 5/2014 | Reguera et al. |
| 8,846,890 | B2 | 9/2014 | Reguera et al. |
| 9,102,521 | B2 | 8/2015 | Lieber et al. |
| 9,234,508 | B2 | 1/2016 | Sahin |
| 9,697,460 | B2 | 7/2017 | Collins et al. |
| 9,784,249 | B2 | 10/2017 | Li |
| 10,083,974 | B1 | 9/2018 | Huang et al. |
| 10,311,357 | B2 | 6/2019 | Nugent et al. |
| 10,388,370 | B2 | 8/2019 | Schmidt et al. |
| 10,684,244 | B2 | 6/2020 | Chen |
| 10,741,778 | B2 | 8/2020 | Kirsch et al. |
| 11,043,265 | B2 | 6/2021 | Li et al. |
| 11,063,227 | B2 | 7/2021 | Kirsch et al. |
| 11,133,058 | B1 | 9/2021 | Philip et al. |
| 2006/0113880 | A1 | 6/2006 | Pei |
| 2007/0157967 | A1 | 7/2007 | Mershin et al. |
| 2008/0283799 | A1* | 11/2008 | Alden .................. C30B 29/60 252/500 |
| 2009/0188784 | A1 | 7/2009 | Lee |
| 2010/0119879 | A1 | 5/2010 | Girguis |
| 2012/0053319 | A1 | 3/2012 | Reguera et al. |
| 2014/0239237 | A1* | 8/2014 | Reguera .................. H01B 1/12 252/514 |
| 2014/0330337 | A1 | 11/2014 | Linke et al. |
| 2014/0336357 | A1 | 11/2014 | Reguera et al. |
| 2018/0007819 | A1* | 1/2018 | Vajo .................. B29C 70/62 |
| 2018/0195997 | A1 | 7/2018 | Li et al. |
| 2018/0202964 | A1 | 7/2018 | Alam et al. |
| 2018/0371029 | A1 | 12/2018 | Lovley et al. |
| 2019/0148085 | A1 | 5/2019 | Kim |
| 2020/0090830 | A1 | 3/2020 | Lovley et al. |
| 2021/0002332 | A1 | 1/2021 | Malvankar |
| 2021/0070811 | A1 | 3/2021 | Reguera et al. |
| 2021/0336169 | A1 | 10/2021 | Yao et al. |
| 2021/0341406 | A1 | 11/2021 | Yao et al. |
| 2021/0344286 | A1 | 11/2021 | Yao et al. |

FOREIGN PATENT DOCUMENTS

| | | |
|---|---|---|
| KR | 101203181 B1 | 11/2012 |
| KR | 101768665 B1 | 9/2017 |
| WO | 2019144931 A1 | 8/2019 |
| WO | 2020069523 A1 | 4/2020 |
| WO | 2021102327 A1 | 5/2021 |

OTHER PUBLICATIONS

Lovley, "e-Biologics: Fabrication of Sustainable Electronics with 'Green' Biological Materials," American Society for Microbiology, May/Jun. 2017, vol. 8, Issue 3 e00695-17.

Reguera et al., "Extracellular electron transfer via microbial nanowires," Nature, Letters, vol. 435, 23, 1098-1101, Jun. 2005.

Vargas et al., "Aromatic Amino Acids Required for Pili Conductivity and Long-Range Extracellular Electron Transport in Geobacter sulfurreducens," mBio, Mar./Apr. 2013, vol. 4, Issue 2 e00105-13.

Adhikari et al., "Conductivity of individual Geobacter pili," RSC Advances., 2016, 6, 8354-8357.

Tan et al., "Synthetic Biological Protein Nanowires with High Conductivity," small 2016, 12, No. 33, 4481-4485.

Tan et al.," Expressing the Geobacter metallireducens PilA in Geobacter sulfurreducens Yields Pili with Exceptional Conductivity," American Society for Microbiology, Jan./Feb. 2017, vol. 8, Issue 1 e02203-16.

Walker et al., "Electrically conductive pili from pilin genes of phylogenetically diverse microorganisms," The ISME Journal (2018) 12, 48-58.

Miaudet et al, "Thermo-electrical properties of PVA-nanotube composite fibers," Elsevier, ScienceDirect, Polymer 48 (2007) 4068-4074.

Byrne et al., "Recent Advances in Research on Carbon Nanotube-Polymer Composites," Advanced Materials, 2010, 22, 1672-1688.

Tseng et al.,"Digital memory device based on tobacco mosaic virus conjugated with nanoparticles," nature nanotechnology, vol. 1., Oct. 2006, pp. 72-77.

Chandrakishore et al., "Facile synthesis of carbon nanotubes and their use in the fabrication of resistive switching memory devices," RSC Advances, 2014, 4, 9905-9911.

Guo et al., "Flexible transparent conductors based on metal nanowire networks," Elsevier, Materials Today, vol. 18, No. 3, Apr. 2015.

Li et al., "Ordered multiphase polymer nanocomposites for high-performance solid-state supercapacitors," Elsevier, Composites: Part B 71 (2015), 40-44.

Sun et al.,"Flexible polydimethylsiloxane/multi-walled carbon nanotubes membranous metacomposites with negative permittivity," Elsevier, Polymer 125 (2017) 50-57.

Green et al., "Conductive Hydrogels: Mechanically Robust Hybrids for Use as Biomaterials," Macromolecular Bioscience, 2012, 12, 494-501.

Liu et al., "Flexible supercapacitor sheets based on hybrid nanocomposite materials," Elsevier, Nano Energy (2013) 2, 133-137.

Tang et al., "Effect of pH on Protein Distribution in Electrospun PVA/BSA Composite Nanofibers," 2012 American Chemical Society, 1269-1278.

Malvankar et al., "Tunable metallic-like conductivity in microbial nanowire networks," Nature Nanotechnology vol. 6, Sep. 2011.

Bauhofer et al., "A review and analysis of electrical percolation in carbon nanotube polymer composites," Elsevier, Composites Science and Technology 69 (2009) 1486-1498.

Balberg et al., "Excluded volume and its relation to the onset of percolation," Physical Review B, vol. 30, No. 7, Oct. 1, 1984.

Celzard et al., "Critical concentration in percolating systems containing a high-aspect-ratio filler," Physical Review B, vol. 53, No. 10, Mar. 1, 1996.

Malhofer et al., "Direct visualization of percolation paths in carbon nanotube/polymer composites," Elsevier, Organic Electronics 45 (2017) 151-158.

Žeželj et al., Publisher's Note: From percolating to dense random stick networks: Conductivity model investigation [Phys. Rev. B 86, 134202 (2012)], Physical Review B 86, 139904(E) (2012).

Malvankar et al., "Structural Basis for Metallic-Like Conductivity in Microbial Nanowires," Mar./Apr. 2015 mBio vol. 6 Issue 2 e00084-15.

Gangopadhyay et al., "Polyaniline-poly(vinyl alcohol) conducting composite: material with easy processability and novel application potential," Elsevier, Synthetic Metals 123 (2001) 21-31.

Zhang et al., "Composite films of nanostructured polyaniline with poly(vinyl alcohol)," Elsevier, Synthetic Metals 128 (2002) 83-89.

Cho et al.,"Synthesis and electrical properties of polymer composites with polyaniline nanoparticles," Elsevier, Materials Science and Engineering C 24 (2004) 15-18.

Ogura et al.,"A Conductive and Humidity-Sensitive Composite Film Derived from Poly(o-phenylenediamine) and Polyvinyl Alcohol," J. Electrochem. Soc., vol. 142, No. 9, Sep. 1995.

Makhlouki et al., "Transport Properties in Polypyrrole-PVA Composites: Evidence for Hopping Conduction," Journal of Applied Polymer Science, vol. 44, 443-446 (1992).

Chen et al., "Electrical Conductivity of Polymer Blends of Poly(3,4-ethylenedioxythiophene) : Poly (styrenesulfonate) :N-Methyl-2-pyrrolidinone and Polyvinyl Alcohol," Journal of Applied Polymer Science, vol. 125, 3134-3141 (2012).

(56) References Cited

OTHER PUBLICATIONS

Zhang et al., "Electrical and dielectric behaviors and their origins in the three-dimensional polyvinyl alcohol/MWCNT composites with low percolation threshold," Elsevier, Carbon 47 (2009) 1311-1320.
Amrin et al., "Electrical properties and conduction mechanism in carboxylfunctionalized multiwalled carbon nanotubes/poly(vinyl alcohol) composites," J Mater Sci (2016) 51:2453-2464.
Yang,"Synthesis and characterization of the cross-linked PVA/TiO2 composite polymer membrane for alkaline OMFC," Elsivier, Journal of Membrane Science 288 (2007) 51-60.
Childers et al., "Geobacter metallireducens accesses insoluble Fe(III) oxide by chemotaxis" Nature, vol. 416, Apr. 18, 2002, pp. 767-769.
Coppi et al., "Development of a Genetic System for Geobacter sulfurreducens", Applied and Environmental Microbiology, vol. 67, No. 7, Jul. 2001, pp. 3180-3187.
Liu et al., "A Geobacter sulfurreducens Strain Expressing Pseudomonas aeruginosa Type IV Pili Localizes OmcS on Pili but Is Deficient in Fe(III) Oxide Reduction and Current Production", Applied and Environmental Microbiology, vol. go, No. 3, Feb. 2014, pp. 1219-1224.
Lovley et al., "Seeing is believing: novel imaging techniques help clarify microbial nanowire structure and function", Environmental microbiology, vol. 17, Issue 7, 2015, pp. 2209-2215.
Malvankar et al., "Tunable metallic-like conductivity in microbial nanowires", Nature Nanotechnology, vol. 6, Sep. 2011, pp. 573-579.
Malvankar et al., "Microbial Nanowires: a New Paradigm for Biological Electron Transfer and Bioelectronics", ChemSusChem Concepts, vol. 5, 2012, pp. 1039-1046.
Malvankar et al., "Microbial nanowires for bioenergy applications", Current Opinion in Biotechnology, vol. 27, 2017, pp. 88-95.
Malvankar et al., Visualization of charge propagation along individual pili proteins using ambient electrostatic force microscopy Nature Nanotechnology, vol. 9, Dec. 2014, pp. 1-10.
Malvankar et al., "Structural Basis for Metallic-Like Conductivity in Microbial Nanowires", mBio, vol. 4, Issue 2, Mar./Apr. 2015, pp. mBio 6:e00084-00015.
Malvankar et al., "Lack of cytochrome involvement in long-range electron transport through conductive biofilms and nanowires of Geobacter sulfurreducens", Energy & Environmental Science, vol. 5, 2012, pp. 8651-8686.
Nevin et al., "Anode Biofilm Transcriptomics Reveals Outer Surface Components Essential for High Density Current 14 Production in Geobacter sulfurreducens Fuel Cells", Plos One, vol. 4, Issue 5, May 2009, pp. 1-11.
Nevin et al., "Power output and columbic efficiencies from biofilms of Geobacter sulfurreducens comparable to mixed 15 community microbial fuel cells", Environmental Microbiology, vol. 10, No. 10, 2008, pp. 2505-2514.
Reardon et al., "Structure of the Type IVa Major Pilin from the Electrically Conductive Bacterial Nanowires of Geobacter sulfurreducens", Journal of Biological Chemistry, vol. 288, No. 41, 2013, pp. 29260-29266.
Richter, "Mutational Analysis of Geopilin Function in Geobacter Sulfurreducens", 2011,[retrieved on line Dec. J8, 2016] at <http://scholarworks.umass.edu/open_access_dissertations/378/], 157 pages.
Shih et al., "Tryptophan-Accelerated Electron Flow Through Proteins", Science, vol. 320, Jun. 27, 2008, pp. 1760-1762.
Ueki T., et al., Decorating the Outer Surface of Microbially Produced Protein Nanowires with Peptides, ACS Synth Biol. Aug. 16, 2019;8(8):1809-1817.
Ueki T., et al., An *Escherichia coli* Chassis for Production of Electrically Conductive Protein Nanowires, ACS Synth Biol. Mar. 20, 2020;9(3):647-654.
Liu X., et al., "Power Generation from Ambient Humidity Using Protein Nanowires," Nature; 578: 550-554 (2020).
Lovley,D., et al, "Geobacter Protein Nanowires", Front. Microbiol. 10, 2078 (2019).
Adhikari, R. Y., et al., Conductivity of individual Geobacter pili, RSC Adv. 6, 8354 (2016).
Milano, Gianluca, et al, "Self-limited single nanowire systems combining all-in-one memristive and neuromorphic functionalities", Dec. 2018, Nature Communications, Article No. 5151. pp. 1-10 (Year: 2018).
Fu, Tianda, et al, "Bioinspired bio-voltage memristors", Nature Communications, 2020, Article pp. 1-10 (Year: 2020).
Kumar, Anish, et al, "Protein Biosensors Based on Polymer Nanowires, Carbon Nanotubes and Zinc Oxide Nanorods", Sensors Journal, May 2011, 5087-5111 (Year: 2011).
Zhou, Jiangfeng, et al, "Development of nanowire-modified electrodes applied in the locally enhanced electric field treatment (LEE FT) for water disinfection", 2020, Journals of Materials Chemistry. Article, 12262-12277 (Year: 2020).
Cui, Yi, et al, "Nanowire Nanosensors for Highly Sensitive and Selective Detection of Biological and Chemical Species", Aug. 2021, Science Magazine, vol. 293, pp. 1289-1292. (Year: 2021).

* cited by examiner

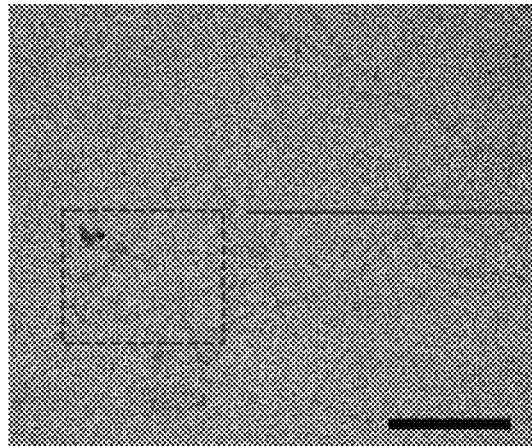
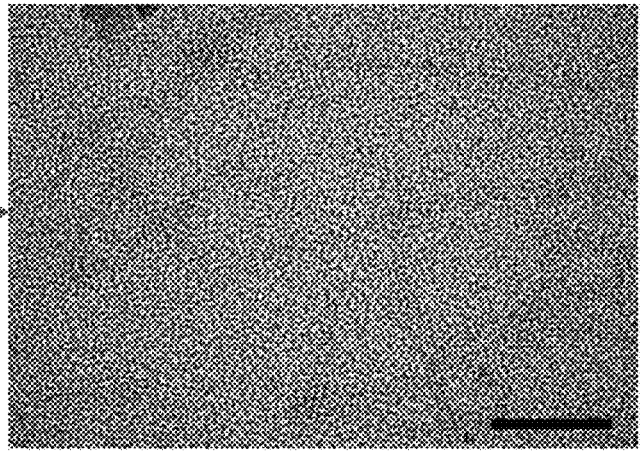
FIG. 4A　　　　　　　　　　　FIG. 4B
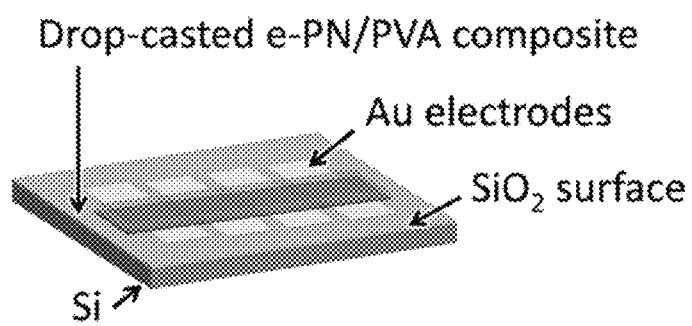
FIG. 5A
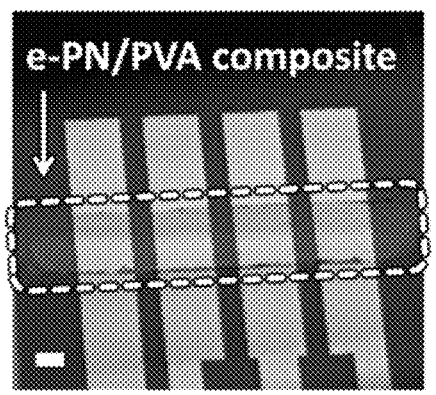
FIG. 5B

CONDUCTIVE COMPOSITE MATERIALS FABRICATED WITH PROTEIN NANOWIRES

This application claims priority to and the benefit of U.S. Provisional Application No. 62/733,496 filed Sep. 19, 2018, which is incorporated herein by reference in its entirety.

TECHNICAL FIELD

The invention relates to electrically conductive materials in general and particularly to electrically conductive protein nanowires and conductive polymeric composites manufactured therefrom.

BACKGROUND

Protein-based electronic materials have substantial potential advantages in sustainability and biocompatibility over electronic materials that are synthesized with harsh chemical processes and/or contain toxic components. The electrically conductive protein nanowires (e-PNs) of the microorganism *Geobacter sulfurreducens* are unique among proteins for their ability to conduct electrons over micron-scale distances. These proteins, which have been referred to as "microbial nanowires" or e-pili in a biological context, show promise as "green" electronic materials, because they can be produced sustainably from inexpensive renewable feedstocks and contain no toxic components. Attractive features of e-PNs include their high aspect ratio (3 nm×10-30 μm) and the fact that their conductivity can be tuned over a wide range ($10^{-6}$ to $10^3$ S·cm$^{-1}$) by genetically tailoring their amino acid sequences.

SUMMARY

In one aspect of the invention there is provided an electronically conductive polymeric composite that includes a polymeric matrix and a plurality of electronically conductive protein nanowires dispersed within the polymeric matrix.

In one embodiment, the protein nanowires are synthesized by the microorganism *Geobacter sulfurreducens*. The protein nanowires may also be protein nanowires produced by a strain of the microorganism *Geobacter sulfurreducens* in which the DNA sequence is modified.

In one embodiment, the protein nanowires are synthesized by the microorganism *Geobacter metallireducens*.

In one embodiment, the protein nanowires are synthesized by the microorganism *Syntrophus aciditrophicus*.

In one embodiment, the protein nanowires are synthesized by the microorganism *Methanospirillum hungatei*.

In one embodiment, the polymeric matrix of the composite includes poly(vinyl alcohol).

In one embodiment, the polymeric matrix includes a siloxane-based polymer. The siloxane-based polymer may be poly(dimethylsiloxane). The siloxane-based polymer may be a functionalized siloxane, wherein the functional groups are selected from among thiol, polyethylene glycol, amine, acrylates, oligopeptides, aromatic groups, and aliphatic chains.

In one embodiment, the weight ratio of e-PN:polymer in the composite may be 0.5% to 10%, or the weight ratio of e-PN:polymer in the composite may be 1.0% to 7.0%.

In one aspect of the invention, there is provided an electrically conductive thin film of a polymeric composite that includes a polymeric matrix and a plurality of electronically conductive protein nanowires dispersed within the polymeric matrix, the thickness of the thin film being in the range of 5 nm to 50 μm.

In one aspect of the invention, there is provided a biosensor made of a polymeric composite that includes a polymeric matrix and a plurality of electronically conductive protein nanowires dispersed within the polymeric matrix. In one embodiment, the biosensor is responsive to changes in pH.

In one aspect of the invention, there is provided a wearable electronic device made of a polymeric composite that includes a polymeric matrix and a plurality of electronically conductive protein nanowires dispersed within the polymeric matrix.

BRIEF DESCRIPTION OF THE DRAWINGS

FIG. 4A is a TEM of 30-nm thick e-PN/PVA composite (weight ratio, e-PNs:PVA=2.8%) fabricated with unstained e-PNs; scale bar=200 nm. FIG. 4B is an enlarged view of marked area in 4A; scale bar=50 nm.

FIG. 5A is a schematic of a drop-cast e-PN/PVA composite sample on an electrode array.

FIG. 5B is a photograph of a composite film with e-PN/PVA fraction of 2.7 wt % on electrode array (scale bar=1 mm).

DETAILED DESCRIPTION

Figure 1:
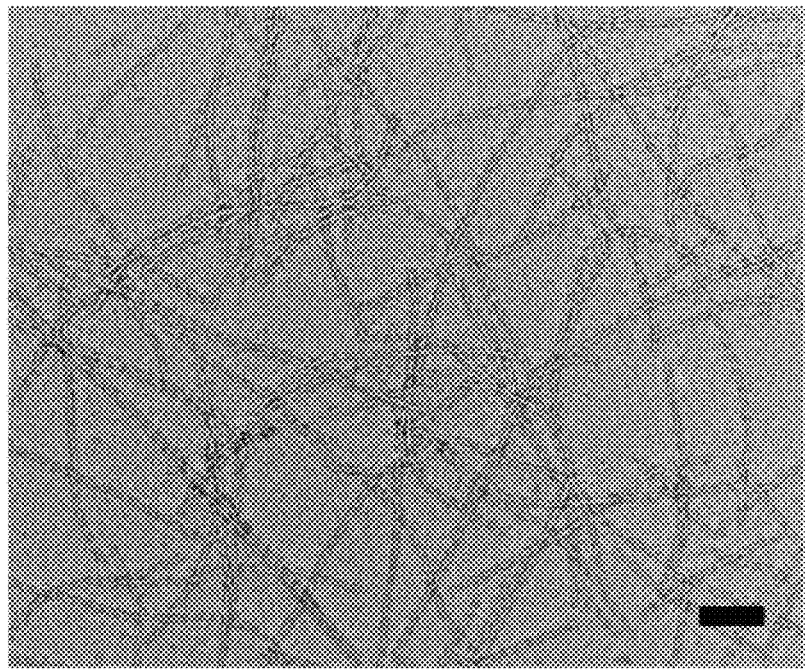
FIG. 1 is a transmission electron micrograph (TEM) of e-PNs after drop casting from aqueous solution and staining with uranyl acetate (scale bar=100 nm).

Protein nanowires are conductive protein filaments produced by the microorganisms, such as *Geobacter sulfurre-* ducens. Initial properties of the microbial nanowires are described in U.S. Pat. No. 7,498,155, which is incorporated by reference herein.

Electrically conductive protein nanowires (e-PNs) are a potential "green" source of electronic materials. It is now understood that microbial nanowires are conductive along their length with a metallic-like conductivity that can be attributed to π-π stacking of aromatic amino acids in the microbial nanowire structure. This property permits the microbial nanowires to propagate charge in a manner comparable to carbon nanotubes with comparable charge densities. The nanowires can also have transistor properties. Other desirable properties include: they are thinner than typical nanowires made from non-biological materials; they conduct electrons over the full length (30 µm) of a single wire or they can be assembled into networks that conduct electrons over centimeter distances; they are produced with a simple "green synthesis" with no toxic chemicals required and no toxic material in the final product; they are very stable, much more difficult to denature than typical proteins; they are robust; then can function over a wide range of pH (2-11); and they function in water.

We integrated *G. sulfurreducens* e-PNs into poly(vinyl alcohol) (PVA) as a host matrix. The resultant e-PN/PVA composites exhibited conductivities comparable to synthetic nanowire/PVA composites. The relationship between e-PN density and conductivity of the composites was consistent with percolation theory. Despite their protein composition, the e-PNs conferred conductivity to the composite at extreme conditions with the highest composite conductivities achieved with e-PNs prepared at pH 1.5 and composite temperatures of 105° C. These results demonstrate that e-PNs are a viable sustainable alternative to other less environmentally friendly nanowire materials for the fabrication of electrically conductive composite materials.

Embedding e-PNs into polymers, as composite materials, allows for the tailoring of electronic performance for a variety of hybrid materials applications, provided the processing conditions are such that the e-PNs maintain their desirable properties in composite structures.

As described herein, protein nanowires naturally produced from *Geobacter sulfurreducens* are integrated into polymeric matrices. Examples of other protein nanowires include the protein nanowires produced by the bacterium *Geobacter metallireducens*. These wires have the same diameter (3 nm) as the *G. sulfurreducens* wires, but are 5,000-fold more conductive. The protein nanowires produced by bacterium *Syntrophus aciditrophicus* may also be used. These wires are only slightly thicker (4 nm) than the *G. sulfurreducens* wires and have similar conductivity. The protein wires produced the archaeon *Methanospirillum hungatei* are of somewhat larger diameter (10 nm) and are more conductive than the *G. sulfurreducens* wires. In addition, the gene for the pilin monomer that *G. sulfurreducens* assembles into protein nanowires can be modified to yield "synthetic protein nanowires" with higher conductivities as described in U.S. Patent Publication No. 2018/0371029A1, which is incorporated herein by reference.

Unlike conventional synthetic nanowires, which strongly aggregate in water, the electronically conductive protein nanowires derived from the anaerobic bacterium *Geobacter sulfurreducens* disperse readily into aqueous medium, which facilitates their incorporation into poly(vinyl alcohol)-based composites.

We have found poly(vinyl alcohol) (PVA) to be a suitable matrix for the fabrication of conductive composites with other microbial nanowire materials. PVA is biocompatible; possesses physical/mechanical properties suitable for advanced processing techniques (such as electrospinning); and is useful as a matrix for diverse electronic materials applications, including resistance-switching memory, flexible transparent electronics and supercapacitors.

Other suitable polymers include siloxane-based polymers, which possess attractive properties for combination with e-PNs to produce composite electronic materials, including their flexibility, ability to withstand large deformations before rupture, temperature stability, biocompatibility, and resistance to chemical degradation. For example, siloxane polymers such as poly(dimethylsiloxane) (PDMS) and a variety of functionalized forms of siloxane polymers, such as those according to Formula I below, have been found to be suitable.

Formula I

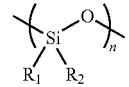

wherein $R_1$ and/or $R_2$ are selected from among various alkyl, aromatic or organic functional groups, such as:

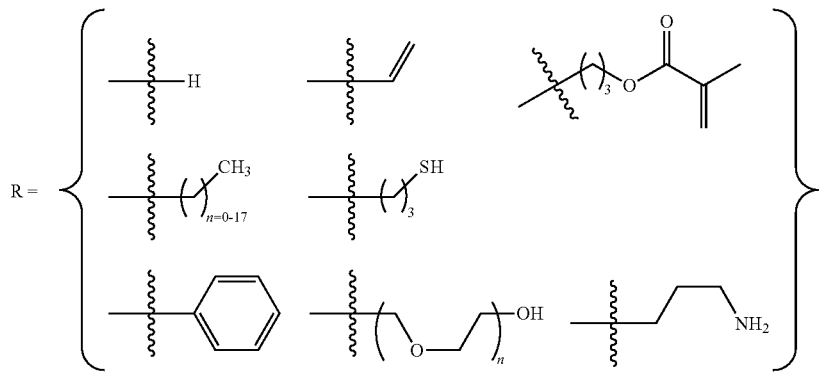

Some functional siloxanes are available commercially and others are prepared by ring-opening polymerization or copolymerization of substituted cyclic siloxane monomers, such as 1,3,5-trimethyl-1,3,5-trivinylcyclotrisiloxane; after polymerization, conversion of the pendent vinyl groups to other functionality is achieved easily. This gives a wide range of functionalized siloxane polymers for combination with e-PNs, including those containing thiols, PEG, amines, acrylates, oligopeptides, aromatic groups, aliphatic chains, and other reactive or inert functionality.

Composites than include e-PNs within flexible siloxane polymer matrices can be accomplished by a variety of processing techniques, including drop casting of films onto a substrate as well as gelation of siloxane precursors, such as the commercially available Sylgard 184. Rapid evaporation of solvent from e-PN/siloxane mixtures on a substrate, followed by thermal- or photo-curing, produces the desired e-PN-filled polymeric siloxanes with tunable film thickness (from 10 nm to microns) and low surface roughness. Removal of the films from the substrate is readily enabled by surface treatment prior to casting, either by spincoating a sacrificial layer or with commercially available release agents.

Fabrication of e-PN/PVA Composites:

To fabricate e-PN/PVA composites, e-PNs were sheared from cells of *Geobacter sulfurreducens*, purified, and suspended in water. FIG. 1 is a transmission electron micrograph (TEM) of e-PNs after drop casting from an aqueous solution and staining with uranyl acetate (scale bar=100 nm).

Figure 2:
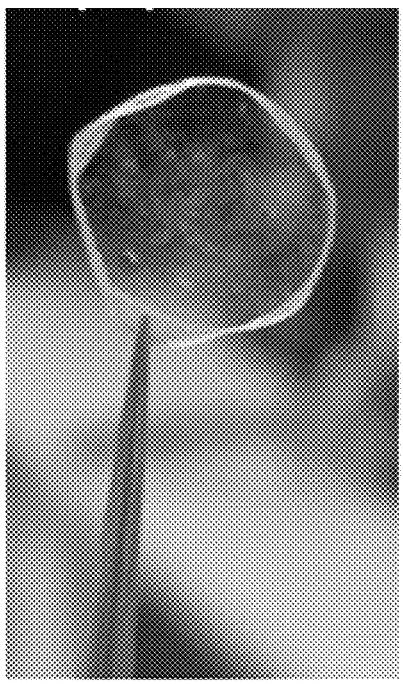
FIG. 2 is a photograph of an exemplary self-standing e-PN/PVA composite film (weight ratio, e-PNs:PVA=1.5%), diameter 90 μm.

The water was evaporated and the e-PNs were re-suspended in an aqueous PVA solution (20 mg/ml) to yield e-PN/PVA suspensions at various concentrations. As shown in FIG. 2, the e-PN/PVA suspensions were drop-cast into molds to yield self-standing composite films. In one embodiment, the weight ratio of e-PNs:PVA was 1.5%, and the diameter of the composite film was 90 μm.

Figure 3:
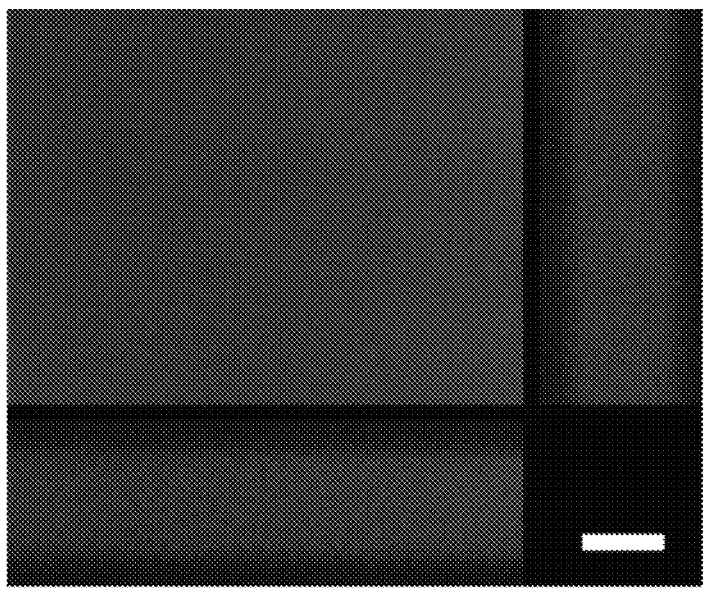
FIG. 3 is a fluorescence confocal micrograph image of an e-PN/PVA composite fabricated with FITC-labeled e-PNs (square area is top view; rectangular areas are side views; scale bar=25 μm).

The e-PNs pre-stained with fluorescein 5-isothiocyanate (FITC) appeared to be homogeneously distributed throughout the composite. FIG. 3 is a fluorescence confocal micrograph image of an exemplary of e-PN/PVA composite fabricated with FITC-labeled e-PNs (square area is top view; rectangular areas are side views; scale bar=25 μm). This uniform distribution was further confirmed with transmission electron microscopy of e-PN/PVA composites produced with unstained e-PNs. FIG. 4A is a TEM of 30-nm thick e-PN/PVA composite (weight ratio, e-PNs:PVA=2.8%) fabricated with unstained e-PNs (scale bar=200 nm). FIG. 4B is an enlarged view of marked area in FIG. 4A (scale bar=50 nm).

The current-voltage (I-V) response of the e-PN/PVA composites was measured for a drop-cast e-PN/PVA composite spanning gold electrode arrays separated by 1 mm non-conducting silicon dioxide gaps, as shown schematically in FIG. 5A. FIG. 5B shows an exemplary composite film with e-PN/PVA fraction of 2.7 wt % on electrode array (scale bar=1 mm).

Figure 6:
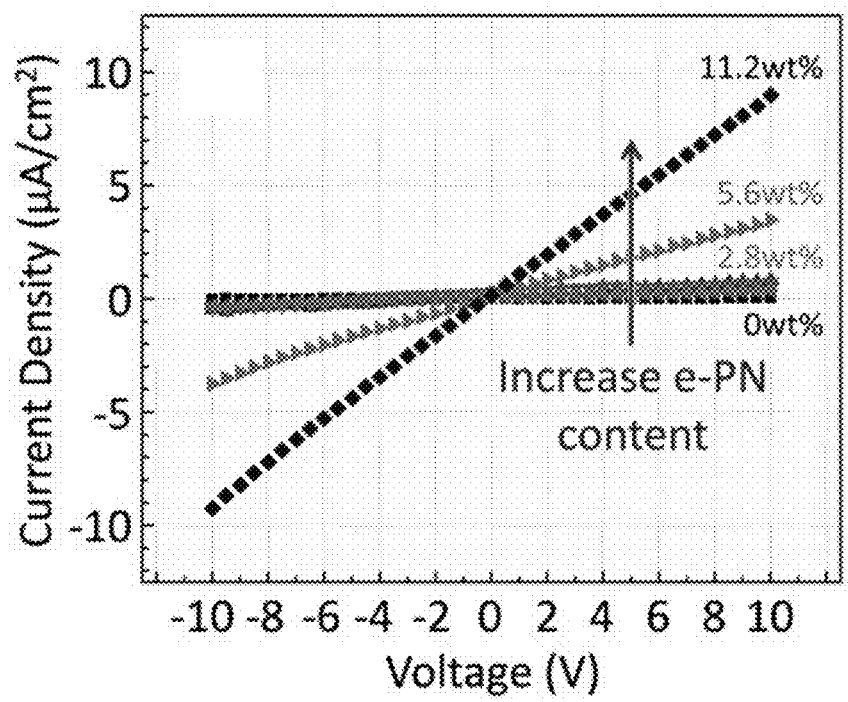
FIG. 6 is a graph showing the current-voltage response of e-PN/PVA composites with increasing e-PN concentrations (in air; 20° C.; relative humidity, 25%).
Figure 7:
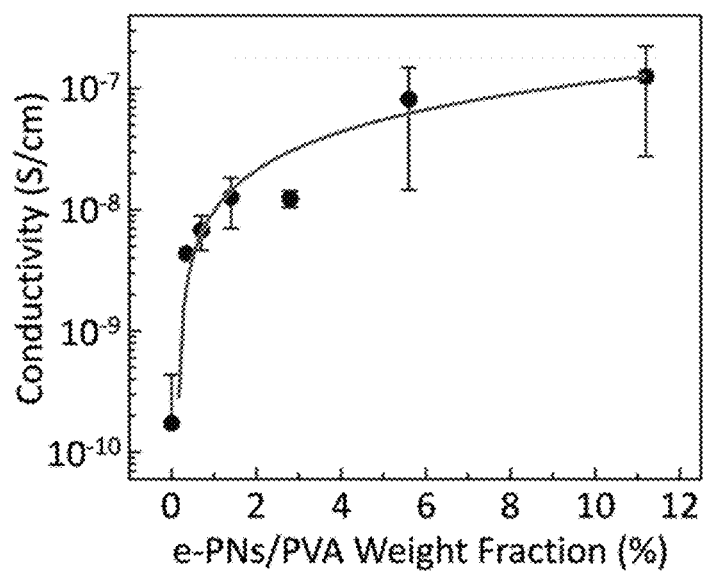
FIG. 7 is a graph showing conductivity versus e-PN/PVA weight fraction in the composites. The reported results are the means and standard deviations of triplicate films measured at each weight fraction.

Current-voltage response of e-PN/PVA composites with increasing e-PN concentrations (in air; 20° C.; relative humidity, 25%) was measured. As shown in FIG. 6, the current density was linear over a voltage range of −10 to 10V. This result demonstrates an ohmic contact between the composite and the electrode and is consistent with the previously reported ohmic response of individual e-PNs and e-PN networks. The conductivity versus e-PN/PVA weight fraction in the composites was measured. As shown in FIG. 7, conductivity increased from $1.75 \times 10^{-10}$ S/cm to $1.26 \times 10^{-7}$ S/cm as the e-PN weight fraction was increased from 0 to 11.2 wt %. The higher composite conductivity values approached those previously reported for e-PN networks in the absence of an insulating polymer.

According to percolation theory for composite systems, the relationship between conductivity (σ) and e-PN fraction is described by:

$$\sigma = \sigma_0 \cdot (\varphi - \varphi_c)^t, \quad (1)$$

where $\sigma_0$ is a constant; φ is the e-PN:PVA weight fraction; $\varphi_c$ is the percolation-threshold weight fraction of the nanowires; and t is the critical exponent. For randomly oriented, high aspect ratio (η) nanowires, the theoretical value of $\varphi_c$ is approximately 1/η. For the e-PNs used in these studies, η is ca. 330-660, yielding a predicted theoretical $\varphi_c$ of 0.15-0.30 wt %. The best fit of the experimental data yielded an estimate of $\varphi_c$ of ~0.2 wt % e-PNs (FIG. 7). The equivalence of the experimental and theoretical value suggested good e-PN miscibility in the PVA matrix.

Theoretical values for tin films are typically ~1.3. The best fit of the e-PN/PVA data (FIG. 2d) gave t of ~1.0. Many factors may influence deviations in t from theoretical values and it is not yet fully understood why the experimental t value is lower than the theoretical prediction, in part because the mechanisms for electron propagation along e-PNs are still poorly understood. As a comparison, t for CNT/PVA composites ranges from 0.9 to 7.6.

Figure 8:
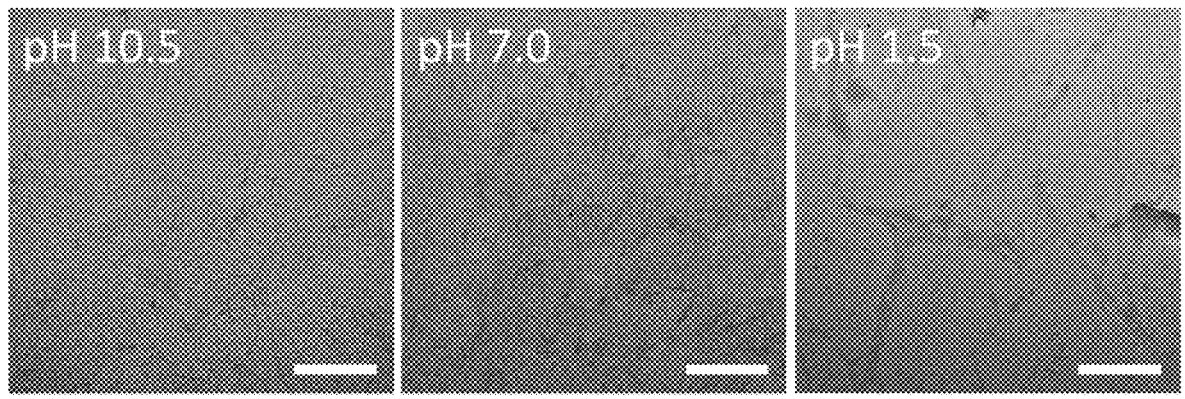
FIG. 8 includes transmission electron micrographs demonstrating the dispersion of e-PNs in 30-nm thick e-PN/PVA composite films fabricated with e-PNs suspended in buffers as a function of the pH of the solution in which the composites were prepared (e-PN/PVA fraction, 3 wt %) scale bars, 500 nm.
Figure 9:
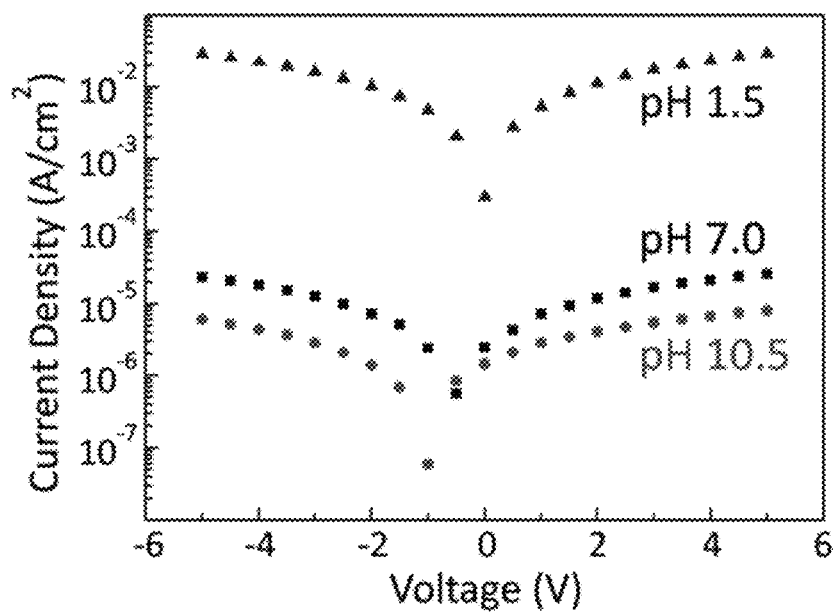
FIG. 9 is a graph showing current density vs voltage for e-PN/PVA composite films across 1-mm-gapped gold electrodes (in air; 20° C.; relative humidity, 25%; e-PN/PVA weight fraction 5.6%).
Figure 10:
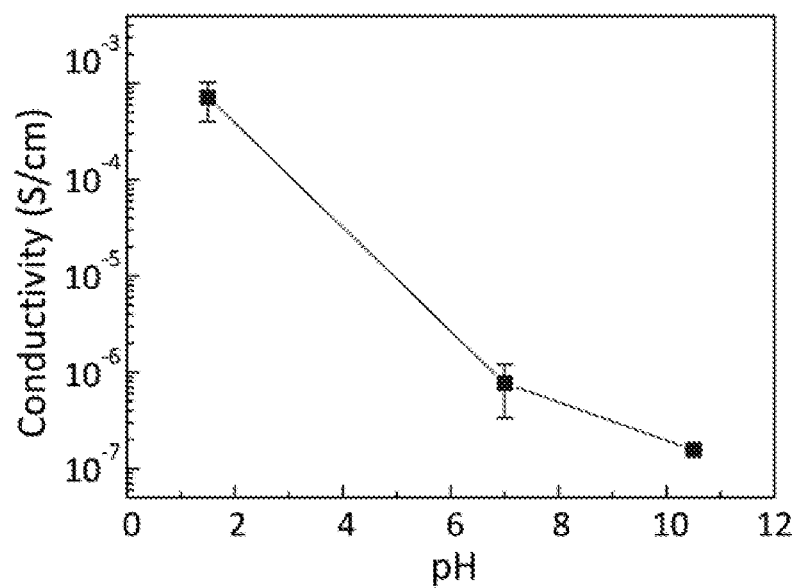
FIG. 10 is a graph showing conductivity of composites versus pH, means and standard deviations of triplicate films at each pH.

The conductivity of *Geobacter* e-PNs increases as the pH of the buffer in which the e-PNs are prepared decreases. This is associated with an increase in the π-π stacking of aromatic amino acids. To determine the conductivity-pH response of e-PN/PVA composites, e-PNs were prepared at pH 1.5, 7.0, or 10.5 and suspended in PVA. FIG. 8 includes transmission electron micrographs demonstrating the dispersion of e-PNs in 30-nm thick e-PN/PVA composite films fabricated with e-PNs suspended in buffers at the designated pH (e-PN/PVA fraction, 3 wt %) (scale bars, 500 nm). Current density versus voltage for e-PN/PVA composite films across 1-mm-gapped gold electrodes was measured (in air; 20° C.; relative humidity, 25%; e-PN/PVA weight fraction 5.6%). As shown in FIGS. 9 and 10, the conductivity of the composite materials increased more than three orders of magnitude, from $1.6 \times 10^{-7}$ S·cm$^{-1}$ at pH 10.5 to $7.1 \times 10^{-4}$ S·cm$^{-1}$ at pH 1.5. The finding that the pH response of e-PN networks is maintained in composites indicates that e-PN composite materials have utility as pH sensors.

Figures 11A, 11B, 11C:
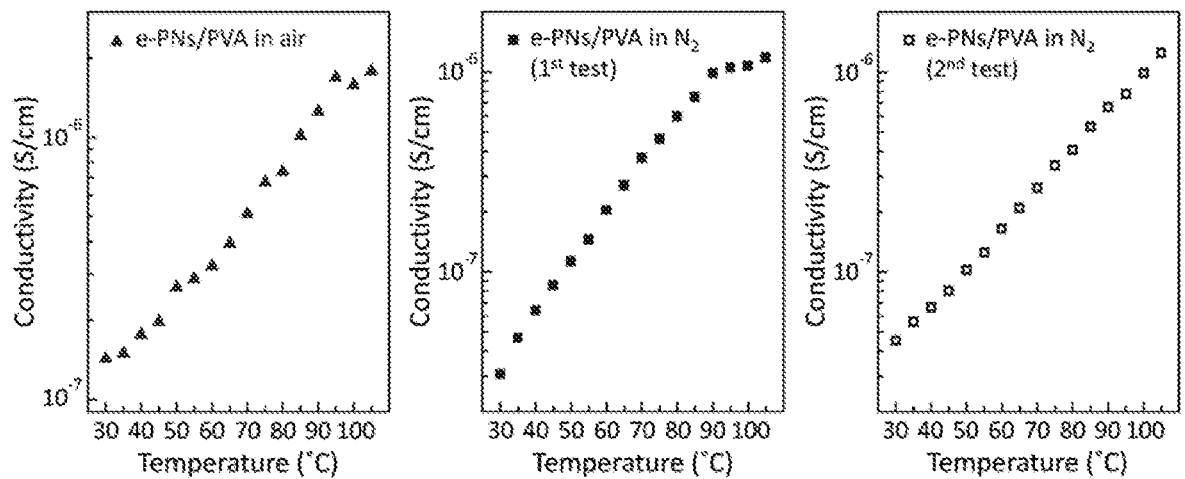
FIGS. 11A 11B and 11C are graphs showing the effect of temperature on e-PN/PVA composite conductivity.

The thermal stability of the e-PN/PVA composites was also investigated. The conductivity of e-PN/PVA composites increased with temperature, whether they were maintained under air or first dried under vacuum at room temperature and stored under $N_2$. FIG. 11A shows that conductivity of the e-PN/PVA composite (e-PNs/PVA fraction 11.2 wt %) in air (relative humidity, 25%) as the temperature was increased 1° C. per min). FIG. 11B shows the same composition e-PN/PVA composite maintained under dry $N_2$ (relative humidity≤1%). FIG. 11C shows the response to second heating cycle after composite in FIG. 11B was cooled to 30° C. There was little change in the conductivity of pure PVA with heating, demonstrating that the conductivity increase was associated with the e-PN network. The conductivity of dried e-PN/PVA composites maintained under $N_2$ was lower than the composites maintained in air, especially at the higher temperatures, indicating that the water content of the composites influenced conductivity.

Figure 12:
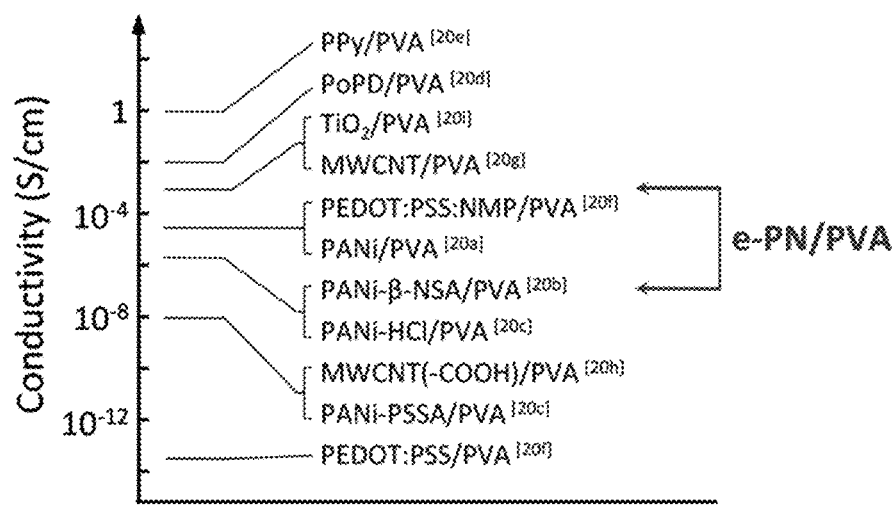
FIG. 12 is chart showing a comparison of the conductivity of diverse PVA composites containing various nanofillers at ca. 5 wt % with e-PN/PVA composites (e-PN wt %=5.6%).

When the e-PN/PVA composites maintained under $N_2$ that had been heated to 105° C. were cooled to 30° C., their conductivity was ~50% higher compared with the first heating cycle (FIG. 11C). This response is similar to that previously observed with carbon nanotubes/PVA nanocomposites in which polymer mobility above the glass-transition temperature (~80° C. for PVA) enabled reorganization or enhancement of nanowire connections. These results demonstrate that the e-PNs are stable at high temperatures, despite being comprised of protein, and that the conductivity of the e-PN/PVA composite has a substantial temperature response.

e-PNs derived from *Geobacter sulfurreducens* can be effectively dispersed within a polymer matrix to yield conductive composite materials, combining the desirable "green" electronic properties of e-PNs with the advantageous physical/mechanical properties of a polymer matrix. The attractive properties of these nanocomposites include their aqueous processability, thermal stability, and tunable conductivity. As shown in FIG. 12, the e-PN/PVA composites span a significant portion of the conductivity range previously described for composites comprised of non-biological conductive nanowires/nanotubes dispersed in PVA. Abbreviations: Polyaniline, PANi; β-naphthalene sulfonic acid, β-NSA; poly(styrene sulfonic acid), PSSA; poly(o-phenylenediamine), PoPD; polypyrrole, PPy; poly(3, 4-ethylenedioxythiophene), PEDOT; poly(styrenesulfonate), PSS; n-methyl-2-pyrrolidinone, NMP; multiwalled carbon nanotubes, MWCNT; carboxyl-modified multiwalled carbon nanotubes, MWCNT (—COOH).

e-PNs from another *Geobacter* species that are 5000-fold more conductive than the e-PNs from *G. sulfurreducens* may be used to manufacture conductive polymeric composites. e-PN conductivity can also be dramatically increased with genetic manipulation of the amino acid content of the e-PN monomer peptide.

Whereas synthetic organic materials typically require high temperatures, and/or expensive/toxic reagents for their preparation, e-PNs are produced at room temperature, in bioreactors, from inexpensive feedstocks. e-PNs contain no toxic components and materials discarded after use degrade to benign products or can serve as a feedstock for methane production. e-PNs may be a desirable and effective conductive component for an array of electronic materials including sensors, conducting hydrogels, and flexible bioelectronics.

Figure 13:
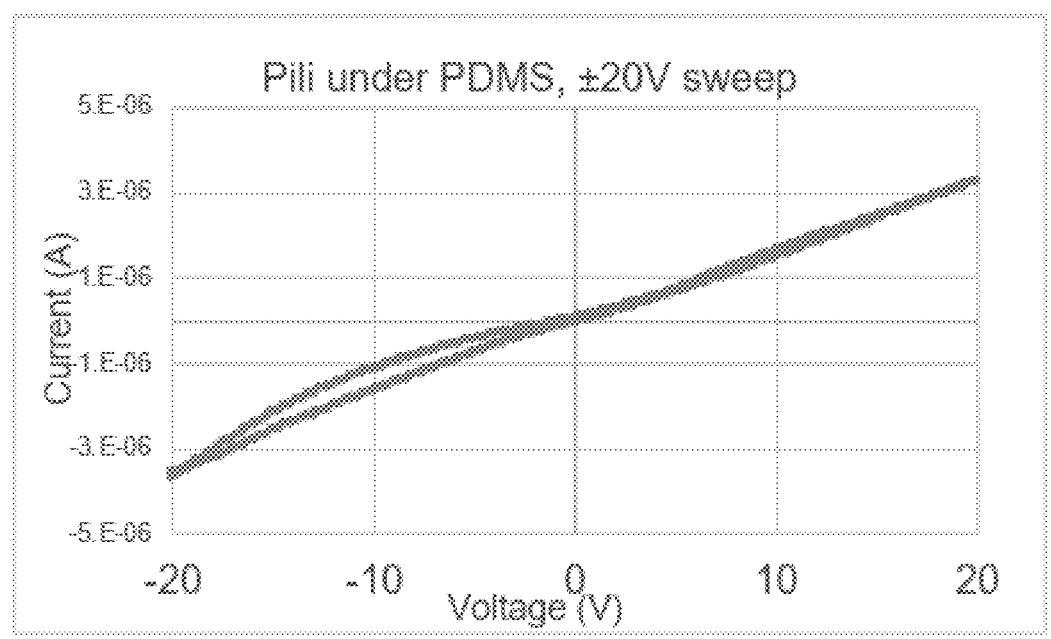
FIG. 13 is a graph showing current-voltage sweeps of e-PN/PDMS composites.

Fabrication of e-PN/PDMS Composites:

Flexible films of e-PNs and polymeric siloxanes can also be formed with a single conductive side. Composites were fabricated using liquid trimethylsilyl-terminated PDMS, in which a solution of 0.30 mg/mL e-PN was concentrated to dryness, after which e-PN solution was added at 3 wt % of the total. The e-PN/polymer composite was heated to 70° C., and the e-PN/siloxane mixture was transferred incrementally. As shown in FIG. 13, consistent conductance ($10^{-7}$ A) was observed from small (±2.5 V) to large (±20 V) sweeps. When the tips were removed from the gold electrodes and placed into direct contact with the PDMS, no conductance was observed (<1 pA).

Similar composite films were prepared from thiol-containing polysiloxanes, by mixing these in solution (such as in THF) with vinyl-functionalized polysiloxanes and a free radical generator such as 2,2-dimethoxy-2-phenylacetophenone (DMPA). This solution drop cast onto substrates at 70° C., on top of the e-PN, then subjected to UV light for cross-linking the thiol- and vinyl-functionalized polymers, producing a cross-linked polysiloxane e-PN composite. Upon testing, it was determined that the UV exposure did not detrimentally impact the electrical conductance of the e-PN. Film thickness was controlled during cure by pinning the pili and siloxanes between glass slides and adjusting the spacer thickness. The integration of e-PN containing unnatural amino acids, or pili derivatives incorporating tailored amounts of natural amino acids, allow for the preparation of new composite e-PN-based structures and their use in bioelectronics applications.

Experimental e-PN/PVA Composites:

Water suspensions of e-PNs harvested from *Geobacter sulfurreducens* and purified were dried in in polypropylene tubes under flowing $N_2$ and resuspended in aqueous solutions of PVA (20 mg/ml to yield the desired weight percent e-PNs). For initial studies of e-PN dispersion, e-PNs were stained with FITC (Fluorescein 5-isothiocyanate, Sigma Aldrich, CAS Number, 3326-32-7) with the protocol for FITC-modification of proteins, provided by the FITC supplier. Residual FITC was removed with dialysis in water.

Microscopy:

e-PNs were examined for purity by staining with uranyl acetate and examining with transmission electron microscopy (TEM). Composites with FITC-stained e-PNs were examined with dark-field confocal laser scanning microscopy (Leica TCS SP5 microscope; Leica Microsystems GmbH) with excitation at 488 nm and an HCX APO 63×(numerical aperture, 0.9) objective. The distribution of unstained e-PNs in PVA was examined with TEM of composites with the same composition that were drop-cast on carbon membrane TEM grids and imaged with a JEOL JEM-2200FS TEM.

Composite Conductivity:

Gold electrodes were fabricated on a 300-nm thick $SiO_2$ layer of heavily doped silicon substrates. After cleaning with a Piranha solution ($H_2SO_4$:$H_2O_2$=3:1) and dilute HF solution, a resist bilayer of LOR5A and positive photoresist S1813 were sequentially spin-coated on the $SiO_2$ surface. Electrode patterns were made via UV exposure with a quartz mask and development in basic developers (Microposit 351 developer (Shipley Company) 5-time diluted with deionized water and RD6 (Futurrex, INC.) sequentially).

The 1-mm-gapped parallel electrodes (100-nm-thick Au on a 5-nm titanium layer) were then thermally deposited in an electron-beam evaporator, followed by an ultrasonication-aided lift-off process in acetone. The gaps were uniform, and resistance measurements confirmed that the electrodes were well insulated from each other. Rectangular widows (2~3-mm-wide) across gold electrodes were oxygen-plasma-treated to produce a hydrophilic zone on which the e-PN/PVAS composites were drop cast. Two-terminal current-voltage (I-V) curve measurements were made with a Keithley 2400 source meter. Conductivity (σ) was calculated as:

$$\sigma = L \cdot I / (T \cdot W \cdot V)$$

where L is the distance between the electrodes; I is the current between electrodes; T is the film thickness, as measured with a scanning profilometer; and the equation W, cross-section width of the film; and V is the voltage across the two electrodes.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. An electronically conductive polymeric composite comprising:
   a polymeric matrix; and
   a plurality of electronically conductive protein nanowires (e-PN) dispersed within the polymeric matrix, a weight ratio of e-PN:polymer in the composite being 0.5% to 10%.

2. The composite of claim 1, wherein the protein nanowires are synthesized by the microorganism *Geobacter sulfurreducens*.

3. The composite of claim 1, wherein the protein nanowires are synthesized by the microorganism *Geobacter metallireducens*.

4. The composite of claim 1, wherein the protein nanowires comprise a strain of the microorganism *Geobacter sulfurreducens* in which the DNA sequence is modified.

5. The composite of claim 1, wherein the protein nanowires are synthesized by the microorganism *Syntrophus aciditrophicus*.

6. The composite of claim 1, wherein the protein nanowires are synthesized by the microorganism *Methanospirillum hungatei*.

7. The composite of claim 1, wherein the polymeric matrix comprises poly(vinyl alcohol).

8. The composite of claim 1, wherein the polymeric matrix comprises a siloxane-based polymer.

9. The composite of claim 8, wherein the polymer comprises poly(dimethylsiloxane).

10. The composite of claim 8, wherein the siloxane-based polymer is a functionalized siloxane, the functional groups are selected from among thiol, polyethylene glycol, amine, acrylates, oligopeptides, aromatic groups, and aliphatic chains.

11. The electronically conductive polymeric composite of claim 1, wherein the weight ratio of e-PN:polymer in the composite is 1.0% to 7.0%.

12. An electrically conductive thin film comprising the composite of claim 1, the thickness of the thin film being in the range of 5 nm to 50 µm.

13. A biosensor comprising a composite according to claim 1.

14. The biosensor of claim 13, wherein the biosensor is responsive to changes in pH.

15. A wearable electronic device comprising the composite of claim 1.

* * * * *